United States Patent
Machida et al.

(10) Patent No.: US 6,569,999 B2
(45) Date of Patent: May 27, 2003

(54) METHOD FOR ACTIVATING DENATURED PROTEIN

(75) Inventors: Sachiko Machida, Tsukuba (JP); Kiyoshi Hayashi, Tsuchiura (JP); Takeshi Takaha, Kobe (JP); Yoshinobu Terada, Nishinomiya (JP); Kazutoshi Fujii, Suita (JP)

(73) Assignee: National Food Research Institute, Ministry of Agriculture, Forestry and Fisheries, Ibaraki (JP)

( * ) Notice: Subject to any disclaimer, the term of this patent is extended or adjusted under 35 U.S.C. 154(b) by 0 days.

(21) Appl. No.: 09/797,971

(22) Filed: Mar. 2, 2001

(65) Prior Publication Data
US 2002/0061568 A1 May 23, 2002

(30) Foreign Application Priority Data
Nov. 21, 2000 (JP) ........................................ 2000-355064

(51) Int. Cl.⁷ .............................. C07K 1/00; C12N 9/00
(52) U.S. Cl. ......................... 530/427; 530/402; 435/183
(58) Field of Search ................................ 530/402, 427; 435/183

(56) References Cited

U.S. PATENT DOCUMENTS 5,563,057 A * 10/1996 Gellman et al. ............ 435/188
5,728,804 A * 3/1998 Sharma et al. .............. 435/188

FOREIGN PATENT DOCUMENTS

JP 2001261697 A * 9/2001 ............ C07K/1/08

OTHER PUBLICATIONS

Daugherty et al., "Arificial Chaperone–Assisted Refolding of Citrate Synthase" (1998) J. Biol. Chem., 273, 33961–33971.*

Silvakana et al., "Artificial Chaperoning of Insulin, Human Carbonic Anhydrase and Hen Egg Lysozyme Using Linear Dextrin Chains—A Sweet Route to the Navtive State of Globular Proteins" (1999) FEBS Lett., 443, 215–219.*

Machida et al., "Cycloamylase as an Efficient Artificial Chaperone for Protein Folding" (2000) FEBS Letters, 486, 131–135.*

* cited by examiner

Primary Examiner—Jon P. Weber
(74) Attorney, Agent, or Firm—Fay, Sharpe, Fagan, Minnich & McKee, LLP

(57) ABSTRACT

A method for activating a denatured protein, includes the steps of: adding a detergent to the denatured protein to allow a protein-detergent complex to be formed; and adding high-molecular weight amylose to the protein-detergent complex so that the high-molecular weight amylose removes the detergent.

17 Claims, 2 Drawing Sheets

Changes in the activation of denatured lysozyme over time using amylose of various molecular weights

METHOD FOR ACTIVATING DENATURED PROTEIN

BACKGROUND OF THE INVENTION

1. Field of the Invention

The present invention relates to a method for activating a denatured protein. In particular, the present invention relates to a method for activating a denatured protein which includes the steps of: adding a detergent to a denatured protein to form a protein-detergent complex; and adding high-molecular weight amylose to the protein-detergent complex so that the high-molecular weight amylose removes the detergent. Moreover, the present invention relates to a protein refolding kit including at least one kind of high-molecular weight amylose and at least one kind of detergent.

2. Description of the Related Art

A protein includes a polypeptide chain consisting of a plurality of L-α-amino acids which are linked via peptide bonds. The order in a sequence of amino acids of a protein is referred to as a primary structure. An actual protein assumes a three-dimensional conformation referred to as a "higher-order structure". In order for a protein to function, it is essential that the protein assumes a proper higher-order structure. Higher-order structures of proteins include secondary structures, tertiary structures, and quaternary structures. Examples of secondary structures include the α helix structure, β sheet structure, and the like. Such secondary structures may be further folded to give tertiary structures. Examples of bonds which make for the stabilization of tertiary structures include hydrophobic bonds, hydrogen bonds, and S—S bonds between cysteine residues. Through the non-covalent association of a plurality of polypeptide chains each assuming a tertiary structure, a quaternary structure results.

A structure which is inherently assumed by a protein molecule under substantially physiological conditions is referred to as a "native" structure. The term "denaturation" refers to the alteration of the physicocheminal properties of a protein from its native state, which may be induced by various factors which cause the destruction of a higher-order structure without causing changes in the primary structure. The destruction of a higher-order structure of a protein may occur due to physical causes, e.g., heating, freezing, irradiation by ultraviolet or X rays, as well as chemical causes, e.g., extremely alkaline conditions, denaturing agents such as organic solvents, urea, and guanidine hydrochloride, or detergents. As a result of denaturation, the structure of a protein may change from a compact structure with orderly folds to an irregular aggregated structure, or a random structure in which the folds have been unfolded. As used herein, a "denatured state" includes both irregularly aggregated states and unfolded states.

A so-called "refolding technique", i.e., a technique for refolding a protein which is in a denatured state as defined above in such a manner as to restore a proper higher-order structure, has very important implications in the industrial utilization of proteins. For example, an enzyme which has been utilized for a certain reaction for producing a substance may be denatured (through heating or the addition of a denaturing agent), whereby its enzyme activity is lost so that the reaction stops; after the resultant product has been recovered, the denatured enzyme may be refolded so as to restore a proper higher-order structure, i.e., activated. Thus, such an enzyme can be put to further reuse.

When heterogeneous proteins are produced in an *E. coli* host, a number of proteins may often become insoluble and inactive substances, referred to as "inclusion bodies". However, with a refolding ability, such an insoluble protein may be first solubilized by a denaturing agent such as urea or guanidine hydrochloride, and thereafter refolded so as to restore a proper higher-order structure, i.e., activated.

The technique of refolding a denatured protein for restoring a proper higher-order structure is associated with two specific problems to be solved: the first problem is how to prevent aggregation of protein; the second problem is how to properly refold the unfolded protein molecules back into a protein.

In the in-vivo folding of a protein, a class of assisting proteins, termed "molecular chaperons", are known to be involved in the above two steps. Molecular chaperons are proteins which bind to a protein which has just been synthesized so that the protein is prevented from being folded in an irregular manner and can be readily transported, and/or assist in the folding process of proteins which would otherwise have difficulties in folding.

A "nascent protein" is a protein which has just been translated in vivo and has not assumed a proper higher-order structure. Immediately after the completion of translation, a nascent protein is bound by a class of molecular chaperons called DnaJ, etc. These molecular chaperons operate upstream of the folding process so as to prevent nascent protein from aggregating or assuming abnormal structures. Thereafter, another molecular chaperon called GroE, which operates downstream of the folding process, acts on the nascent protein. Owing to the action of GroE, the nascent protein gradually begins to assume a proper higher-order structure, until it is finally folded, into an active protein. In the course of the folding process, the molecular chaperons which assisted in the folding leave the nascent protein.

In recent years, several attempts have been made to construct artificial chaperons with a view to reproducing the in-vivo functions of molecular chaperons In vitro (e.g., in a test tube) and restoring the activity of a denatured protein in vitro. Daugherty et al. (J. Biol. Chem., 273,3961–33971 (1998)) reported a method of refolding a denatured protein by using artificial chaperons. The reported method employs a non-ionic detergent designated Triton X-100, and a polyoxyethylene-type detergent having a short alkyl group chain, as artificial chaperons which function to prevent aggregation of proteins. After a protein-detergent complex is formed by using these artificial chaperons, β cyclodextrin (hereinafter abbreviated as "β CD"), which is a low-molecular weight cyclic α-1,4-glucan, is added as a substance (hereinafter also referred to as a "detergent removing agent") for causing removal of the detergents. Thus, the detergents are gradually removed from the protein-detergent complex, thereby allowing the denatured protein to naturally assume a higher-order structure.

Thereafter, Silvakama Sundari et. al (FEBS Lett., 443, 215–219 (1999) ) discloses that, not only a low-molecular weight cyclic α-1,4-glucan (cyclodextrin), but also a low-molecular weight straight-chain α-1,4-glucan can be effective as a substance for causing gradual removal of detergents from a protein-detergent complex in a similar artificial chaperon system.

More recently, Machida et al. (Japanese Patent Application No. 2000-71533) is a study specifically into the effects of various combinations of detergents and detergent removing agents on the restoration of the activity of three different proteins in a similar artificial chaperon system, reporting the following results:

(1) High-molecular weight cyclic α-1,4-glucan (having a polymerization degree of about 40 to about 150)

enables faster and more effective restoration of protein activity than low-molecular weight cyclic α-1,4-glucan (having a polymerization degree of about 6 to about 8).

(2) Each protein may have its activity restored to various degrees depending on the detergents and the detergent removing agents used. Therefore, for a higher level restoration of activity, it is essential to select appropriate combinations of detergents and detergent removing agents in accordance with the protein to be restored.

Thus, it has been indicated that the artificial chaperon technology is very effective for the activation of denatured proteins. On the other hand, it has also been learned that the degree of activity restoration of a denatured protein may substantially vary depending on the detergents and the detergent removing agents used.

A large number of detergents are known in the art to be usable as artificial chaperons.

As for detergent removing agents, high-molecular weight and low-molecular weight cyclic α-1,4-glucans (Japanese Patent Application No. 2000-71533, supra) and low-molecular weight straight-chain α-1,4-glucan (Silvakama Sundari et al., supra) are currently known. These glucans are found to be every effective for the activation of denatured proteins.

Amyloses are commercially available, such as: low-molecular weight amylose (average molecular weights: about 2900), which is obtained by decomposing starch with a debranching enzyme such as isoamylase; and amylose fractions after removing amylopectin from natural starch. Low-molecular weight amylose is not preferably used for the activation of denatured proteins because of its small molecular weight and poor inclusion ability. Amylose fractions are not preferably used for the activation of denatured proteins because of their extremely poor water solubility, high impurity contents (e.g., fat), branch structures associated with α-1,6-bonds, and broad molecular weight distribution.

On the other hand, a similar glucose polymers, α-1,6-glucan, has been shown to have no ability to activate denatured proteins (Silvakama Sundari et al., supra). It has also been indicated that the same cyclic α-1,4-glucan may have different degrees of protein activation action depending on the polymerization degree thereof. That is, a cyclic α-1,4-glucan having a high polymerization degree provides a higher degree of protein activation action than a cyclic α-1,4-glucan having a low polymerization degree (Japanese Patent Application No. 2000-71533, supra).

Thus, it is already known that polymers of glucose may have different degrees of protein activation action depending on the mode of bonding, polymerization degree, and the like. Thus, as for detergent removing agents, there is no adequate understanding as to which substances can be expected to have good effects. Hence, it is difficult for those skilled in the art to select proper detergent removing agents.

While the hitherto undertaken studies find the highest degree of protein activation action in cyclic α-1,4-glucan having a high polymerization degree, such a cyclic α-1,4-glucan having a high polymerization degree is difficult to produce in practice, and has not been trade commercially available yet. Thus, there are some practicality concerns.

Against such a back ground, there is a need for developing a detergent removing agent which has a high activation action on denatured proteins and which has a high practicality. Moreover, there is a need for a useful and highly practical method for activating a denatured protein, where the protein may have e poor spontaneous folding ability and have difficulties in assuming a proper higher-order structure, or even cannot assume a higher-order structure without the assistance of molecular chaperons, such that the protein can be refolded in a relatively short time so as to assume a proper higher-order structure for acquiring activity.

SUMMARY OF THE INVENTION

According to one aspect of the present invention, there is provided a method for activating a denatured protein, including the steps of: adding a detergent to the denatured protein to allow a protein-detergent complex to be formed; and adding high-molecular weight amylose to the protein-detergent complex so that the high-molecular weight amylose removes the detergent.

In one embodiment of the invention, the method further includes the step of adding a denaturing agent to the denatured protein to cause the denatured protein to be in an unfolded state, wherein the step of adding the denaturing agent is performed before the step of adding the detergent to the denatured protein.

In another embodiment of the invention, the high-molecular weight amylose is an inclusion compound which includes a lower alcohol.

In still another embodiment of the invention, the lower alcohol is butanol.

In still another embodiment of the invention, the high-molecular weight amylose has an average molecular weight in the range of about 10,000 to about 20,000,000.

In still another embodiment of the invention, the high-molecular weight amylose has an average molecular weight in the rage of about 20,000 to about 11,000,000.

In still another embodiment of the invention, the high-molecular weight amylose is an amylose which is synthesized by using an enzyme.

In still another embodiment of the invention, the detergent is selected from the group consisting of: polyoxyethylene sorbitan ester, polyoxyethylene dodecyl ether, polyoxyethylene fatty acid ester, sucrose fatty acid ester, cetyltrimethylammonium bromide, sodium deoxycholate, hexadecyltrimethylammonium bromide, and myristylsulfobetaine.

In still another embodiment of the invention, the denatured protein includes an α helix structural region.

In still another embodiment of the invention, the denatured protein includes a β sheet structural region.

In still another embodiment of the invention, the denatured protein includes an intramolecular S—S bond.

According to another aspect of the present invention, there is provided a method for activating a denatured protein including an α helix structural region, including the steps of: adding an excess of a polyoxyethylene type detergent complex to be formed, thereby preventing aggregation of the protein; and adding high-molecular weight amylose to the protein-detergent complex so that the high-molecular weight amylose removes the detergent, thereby allowing the protein to be folded again into a higher-order structure for acquiring activity, thus activating the protein.

In one embodiment of the invention, the polyoxyethylene type detergent is selected from the group consisting of: polyoxyethylene sorbitan ester, polyoxyethylene dodecyl ether,polyoxyethylene fatty acid ester, and sucrose fatty acid ester.

According to yet another aspect of the present invention, there is provided a method for activating a denatured protein including a β sheet structural region, including the steps of: adding an excess of an ionic type detergent to the denatured protein to allow a protein-detergent complex to be formed, thereby preventing aggregation of the protein; and adding high-molecular weight amylose to the protein-detergent complex so that the high-molecular weight amylose removes the detergent thereby allowing the protein to be folded again into a higher-order structure for acquiring activity, thus activating the protein.

According to still another aspect of the present invention, there is provided a method for activating a denatured protein including an intramolecular S—S bond, including the steps of: adding an excess of an ionic type detergent to the denatured protein to allow a protein-detergent complex to be formed, thereby preventing aggregation of the protein; and adding high-molecular weight amylose to the protein-detergent complex so that the high-molecular weight amylose removes the detergent, thereby allowing the protein to be folded again into a higher-order structure for acquiring activity, thus activating the protein.

In one embodiment of the invention, the ionic type detergent is selected from the group consisting of: cetyltrimethylammonium bromide, sodium deoxycholate, hexadecyltrimethylammonium bromide, and myristylsulfobetaine.

In another embodiment of the invention, the ionic type detergent is selected from the group consisting of: cetyltrimethylammonium bromide, sodium deoxycholate, hexadecyltrimethylammonium bromide, and myristylsulfobetaine.

According to still another aspect of the present invention, there is provided a kit for refolding a protein, including at least one kit of high-molecular weight amylose and at least one kit of detergent.

In one embodiment of the invention, the high-molecular weight amylose is an inclusion compound which includes a lower alcohol.

In another embodiment of the invention, the lower alcohol is butanol.

In still another embodiment of the invention, the high-molecular weight amylose has an average molecular weight in the range of about 10,000 to about 20,000,000.

In still another embodiment of the invention, the high-molecular weight amylose has an average molecular weight in the range of about 20,000 to about 11,000,000.

In still another embodiment of the invention, the high-molecular weight amylose is an amylose which is synthesized by using an enzyme.

In still another embodiment of the invention, the detergent is selected from the group consisting of: polyoxyethylene sorbitan ester, polyoxyethylene dodecyl ether, polyoxyethylene fatty acid ester, sucrose fatty acid ester, cetyltrimethylammonium bromide, sodium deoxycholate, hexadecyltrimethylammonium bromide, and myristylsulfobetaine.

After much research effort, the inventors have found that a high-molecular weight amylose, which is a straight-chain α-1,4-glucan having a high polymerization degree, functions, more effectively as a detergent removing agent than a straight-chain α-1,4-glucan having a low molecular weight, and therefore is useful for the efficient activation of a denatured protein. The Inventors further found that a method for activating a denatured protein which employs a high-molecular weight amylose can be generically utilized for various denatured proteins, thereby accomplishing the present invention. High-molecular weight amylose is more practical than high-molecular weight cyclic α-1,4-glucan because high-molecular weight amylose can be supplied in large quantities through synthesis employing phosphorylase.

By combining high-molecular weight amylose and various detergents, a protein refolding kit having a high practicality and generic applicability can be provided according to the present invention.

Thus, the invention described herein makes possible the advantages of (1) providing a method for efficiently activating a denatured protein; and (2) providing a protein refolding kit.

These and other advantages of the present invention will become apparent to those skilled in the art upon reading and understanding the following detailed description with reference to the accompanying figures.

DESCRIPTION OF THE PREFERRED EMBODIMENTS

Hereinafter, the present invention will be described in more detail.

According to the present invention, there is provided a method for activating a denatured protein. The method according to the present invention includes the steps of adding a detergent to a denatured protein to form a protein-detergent complex; and adding a high-molecular weight amylose to the protein-detergent complex so that the high-molecular weight amylose removes the detergent.

Figure 1:
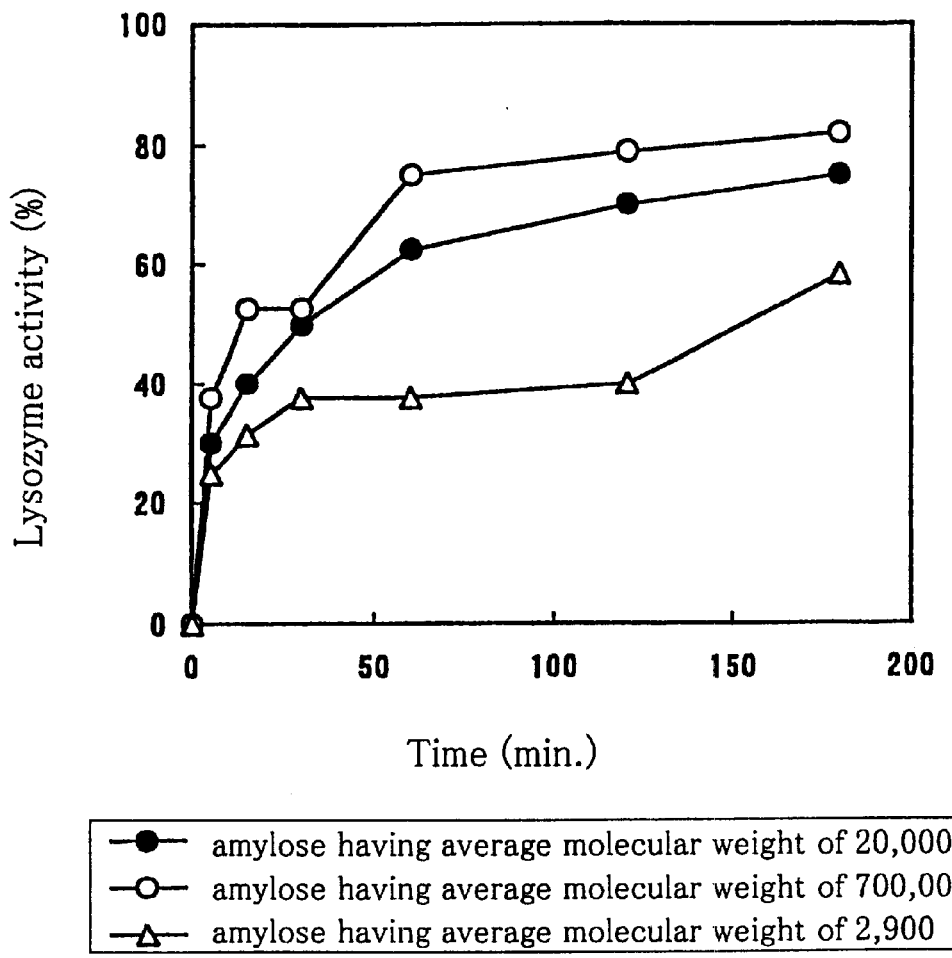
FIG. 1 is a graph illustrating changes in the activation of denatured lysozyme over time using amylose of various molecular weights. The axis of abscissas denotes incubation time with amylose; and the axis of ordinates denotes enzymatic activity of lysozyme. White circles represent an enzymatic activity of lysozyme obtained by using amylose having an average molecular weight of about 700,000; black circles represent an enzymatic activity of lysozyme obtained by using amylose having an average molecular weight of about 20,000; and white triangular represent an enzymatic activity of lysozyme obtained by using amylose having an average molecular weight of about 2,900.
Figure 2:
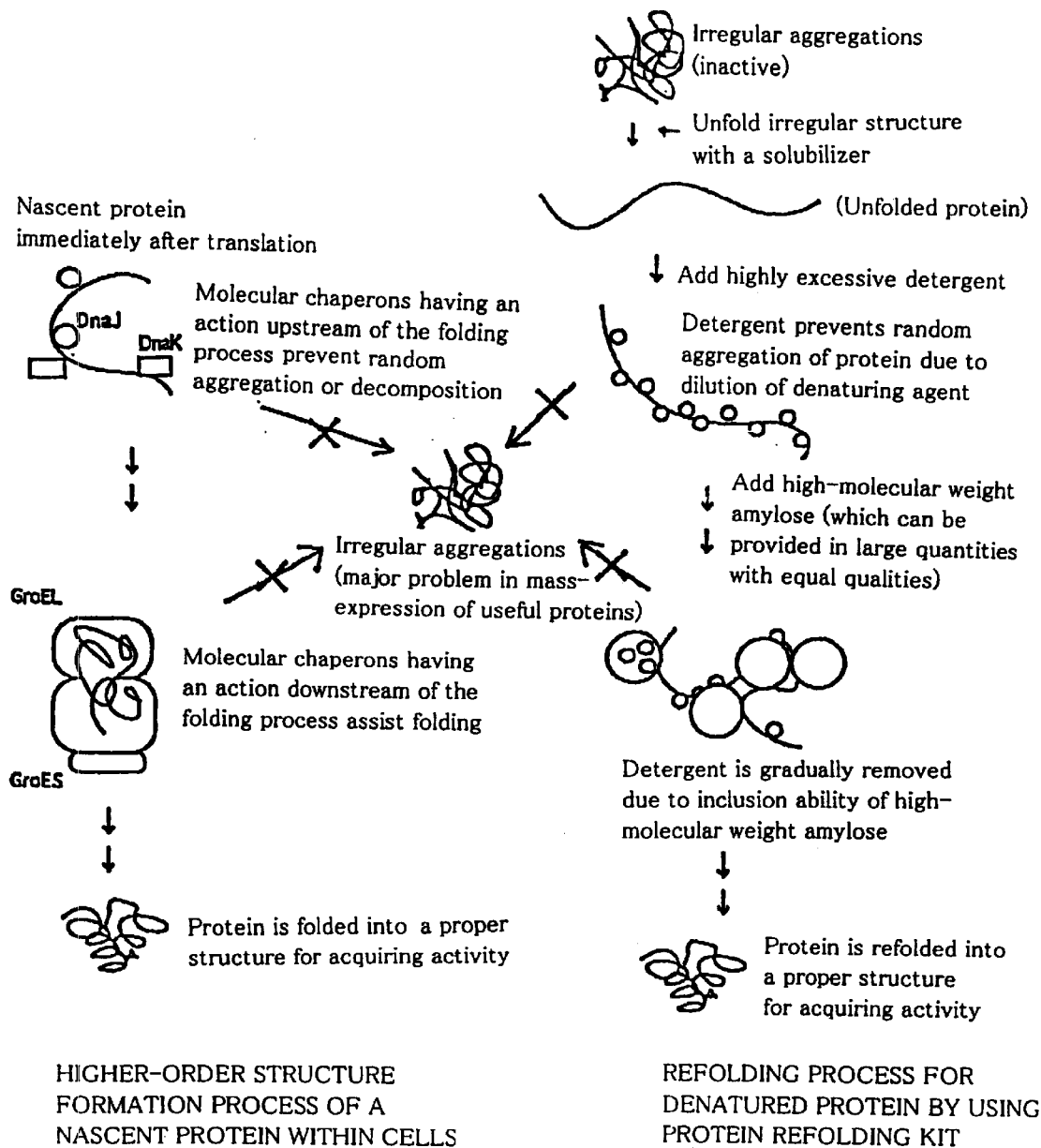
FIG. 2 is a schematic diagram illustrating the activation of a denatured protein by using a method according to the present invention.

FIG. 2 is a schematic diagram illustrating the activation of a denatured protein by using the method according to the present invention.

As used herein, a "denatured protein" means a protein whose higher-order structure(s) has been destroyed while conserving the primary structure of the protein, such that the activity of the protein has been lost or reduced, i.e., a protein whose activity has been reduced to about 90% or less, about 80% or less, about 70% or less, about 60% or less, about 50% or less, about 40% or less, about 30% or less, about 20% or less, or about 10% or less against that of the native state defined as 100%.

The term "denatured protein" encompasses all proteins whose activity has been lost or reduced because of assuming a higher-order structure(s) which is different from the proper higher-order structure. A "higher-order structure different from the proper higher-order structure" may refer to an irregular aggregation state, or an unfolded state. Preferably, the "denatured protein" Is in an unfolded state so as to facilitate binding with detergents.

As used herein, an, "unfolded state" refers to a state where bonds which a protein may have in a native state, e.g., hydrogen bonds, hydrophobic bonds, and Van der Waals force, are destroyed. In one embodiment of the present invention, an "unfolded state" refers to a state in which the rotation angles of bonds within a polypeptide chain of a protein are at angles independent of the amino acid sequence of the polypeptide.

An "aggregated state" refers to a state of a protein having been folded to a higher-order structure(s) which is different from the proper higher-order structure(s), or a number of proteins having aggregated with an improper higher-order structure resulting in a loss or reduction of the activity.

Although there is no limitation as to the denatured proteins to be activated by the method according to the present invention, examples of such denatured proteins include proteins which result from the denaturation of proteins which have an activity in a native state. Examples of "proteins which have an activity in a native state" include enzymes, bioactive polypeptides, and the like.

As used herein, "activation of a denatured protein" refers to the restoration of an activity of a denatured protein. For example, restoration of activity by about 10 or more points is preferable; restoration of activity by about 20 or more points is more preferable; restoration of activity by about 30 or more points is still more preferable; restoration of activity by about 40 or more points is still more preferable; restoration of activity by about 50 or more points is still more preferable. Assuming that at least one bioactivity (e.g., enzymatic activity) which the denatured protein originally possesses in a non-denatured (native) state (defined as 100%) has reduced to less than about 50% as a result of denaturation, "activation of a denatured protein" refers to a restoration of activity to at least about 50%, typically about 60% preferably about 70%, more preferably about 80%, still more preferably about 90%, and most preferably about 100% based on the activity of a native protein, as a result of subjecting the denatured protein to a given treatment.

A native state, a denatured state, and an activated state as mentioned above can be easily determined by activity measurement using various well-known activity measurement methods.

Examples of enzymes include: enzymes for clinical diagnosis, enzymes for use related with drugs, enzymes for food processing, enzymes for detergents, enzymes for fiber processing, enzymes for use related with paper/pulp, enzymes for use related with feeds, enzymes for use related with cosmetics, enzymes for chemical engineering, enzymes for genetic engineering, enzymes for various research purposes, and the like.

Preferably, the enzymes are: oxidoreductases such as glucose oxidase, catalase, and lipoxygenase; hydrolases such as amylase, protease, lipase, and lysozyme: transferases such as aminotransferase, glycosyltransferase, DNA polymerase, end phosphorylase, lyases such as alginate lyase, carbonate dehydrogenase B (hereinafter also abbreviated as "CAB"), and citrate synthase (hereinafter also abbreviated as "CS"); isomerases such as xylose isomerase, and phosphoglucomutase; and synthetases enzymes such as DNA ligase and glutamine synthetase.

More preferably, the enzymes are citrate synthase, carbonate dehydrogenase B, and lysozyme.

Examples of bioactive polypeptides include antibodies, peptide hormones, cytokines, receptor proteins, and the like.

Preferably, the bioactive polypeptides are antibodies; peptide hormones such as insulin, growth hormones, glucagon, angiotensin, and thyroid stimulating hormone; cytokines such as interleukins, interferons, colony-stimulating factors, and tumor necrosis factors; and receptor proteins such as insulin receptors, steroid receptors, and cytokine receptors.

A denatured protein to be used for the activation method according to the present invention may have various secondary structural regions in a native state before denaturation. Examples of secondary structural regions Include an α helix structural region and a β sheet structural region. An example of a structure which stabilizes a tertiary structure is an intramolecular S—S bond. A native protein before denaturation may be substantially entirely composed of an α helix structural region or a β sheet structural region, or may be composed of various ratios of an α helix structural region and a β sheet structural region. Optionally, the native protein before denaturation may include a region having any structure other than the α helix structure or the β sheet structure. Preferably, the native protein before denaturation is a protein which is composed substantially of an α helix structural region or a β sheet structural region. Alternatively, the denatured protein to be used for the activation method according to the present invention may be a protein which in a native state would be stabilized via intramolecular S—S bonds.

The denatured protein may be a denatured protein which has been denatured from a native state by physical causes, e.g., heating, freezing, irradiation by ultraviolet or X rays, or chemical causes, e.g., extremely alkaline conditions or denaturing agents such as organic solvents, urea, and guanidine hydrochloride, or detergents.

In the case where a denatured protein in an aggregated state is to be activated, it is preferable to add a denaturing agent, before the addition of a detergent, to ensure that the structure of the denatured protein has been unfolded.

As used herein, a "denaturing agent" refers to any chemical substance other than detergents which causes denaturation of a protein. Examples of denaturing agents include urea, guanidine hydrochloride, organic solvents, and the like.

As used herein, a "detergent" refers to an amphipathic substance having hydrophilic atomic group and a hydrophobic atomic group within the molecule. The detergent to be used for the activation method according to the present invention may be any detergent. Various cationic detergents, anionic detergents, amphoteric detergents, and non-ionic detergents may be effectively used as a detergent for the activation method according to the present invention. Preferably, the detergent is selected in accordance with the structure assumed by the protein in a native state before denaturation.

For example, for proteins which originally have an α helix structure in a native state before denaturation, non-ionic detergents are preferably used. More preferable are alkylpolyoxyethylene ether type detergents of the general formula $C_nH_{2n-1}(OCH_2CH_2)_xOH$, commonly abbreviated as "CnEx". More preferably, non-ionic detergents such as polyoxyethylene sorbitan ester, polyoxyethylene dodecyl ether, polyoxyethylene heptamethyl hexyl ether, polyoxyethylene fatty acid ester, sucrose fatty acid ester can be especially effectively used. Alternatively, non-ionic detergents such as octylglucoside, heptylthioglucoside, decanoyl-N-methylglucamido may be used.

Among the aforementioned polyoxyethylene type detergents, polyoxyethylene sorbitan ester type detergents are abbreviated as "Cn-sorbitan-Ex". Among polyoxyethylene sorbitan ester type detergents, those whose polyoxyethylene chain length is 4 to 100 are preferable; those whose polyoxyethylene chain length is 4 to 21 are more preferable; and those whose polyoxyethylene chain length is 20 are most preferably used. As used herein, the "length" refers to the repeated number of polyoxyethylene residues —$(OCH_2CH_2)$—. Examples of polyoxyethylene sorbitan ester type detergents whose polyoxyethylene chain length is 4 to 21 include: Tween 20, Tween 40, Tween 60, Tween 80, Tween 21, Tween 61, Tween 81 (commercially available from Atlas Powder, Sigma, and other companies). Examples of polyoxyethylene sorbitan ester type detergents whose polyoxyethylene chain length is 20 include: Tween 20, Tween 40, Tween 60, Tween 80 (commercially available from Atlas Powder, Sigma, and other companies. Among others, Tween 40 and Tween 60, whose alkyl group has a length of 16 and 18, are especially preferable in terms of maintaining proteins in an excellent dispersed state, and hence excellent aggregation prevention effects.

If the polyoxyethylene chain of the polyoxyethylene sorbitan ester type detergent is excessively long or short, the ability to maintain protein in a dispersed state may be weakened, so that the aggregation prevention effect for the protein of interest may be deteriorated.

For those denatured proteins which have at least one of the β sheet structure and intramolecular S—S bonds In a native state, cationic or anionic detergents can be especially effectively used. Examples of cationic detergents include cetyltrimethylammonium bromide, hexadodecyltrimethylammonium bromide (hereinafter also abbreviated as "CTAB"), and the like. Examples of anionic detergents include sodium deoxycholate, 3-[(3-colamidepropyl) dimethylammonio]-1-propanesulfonic acid, myristylsulfobetaine (hereinafter also abbreviated as "SB3-14"), and the like. Cationic detergents are preferable, especially CTAB, SB3-14.

Surfactants are usually dissolved in an appropriate solvent or solution, so as to be used in the form of a solution. A solution for dissolving a detergent therein can be any solution that has a pH level and salt concentration such that proteins are not denatured. The solution is preferably a buffer. As such a buffer, any buffer can be used that does not unfavorably affect the activity and stability of the enzyme or bioactive polypeptide of interest. Examples of buffers include a Tris-sulfate buffer, a Tris-acetate buffer, a phosphate buffer, acetate buffer, and Good's buffer.

The pH range of the solution in which detergents are to be dissolved is typically from about pH 3.0 to about pH 10.0, and more preferably from, about pH 5.0 to about pH 9.0.

The concentration and addition amount of a detergent-containing solution may be arbitrarily selected so long as the detergent concentration after the addition is typically in the range of about 0.0001 wt % to about 5 wt %, preferably in the range of about 0.001 wt % to about 3 wt %; more preferably in the range of about 0.005 wt % to about 2 wt %; and most preferably in the range of about 0.01 wt % to about 1.5 wt %.

A solution, containing a denatured protein and a solution containing a detergent can be mixed by any known method. A detergent may be added to the denatured protein. After the addition, the resultant mixture is gently stirred so as to become substantially homogeneous, as necessary. Thereafter, the mixture is left to stand at an appropriate temperature for an appropriate period of time, as necessary. The mixture is typically left to stand at room temperature for several minutes to several days; preferably about 5 minutes to about 1 day; more preferably about 10 minutes to overnight; and still more preferably for about 1 hour. As used herein, "room temperature" refers to a temperature in the range between about 20° C. to about 25° C. "Overnight" means about 5 to 10 hours.

In general, a denatured protein which has been placed in an unfolded state by a denaturing agent (e.g., guanidine hydrochloride or urea) binding thereto may be refolded into a state assuming a proper higher-order structure (i.e., an active state) in vitro by gradually removing the denaturing agent from the denatured protein bound by the denaturing agent by using means such as dilution, dialysis, or the like, so as to allow the denatured protein to refold and assume a proper three-dimensional conformation. However, problems such as aggregation of proteins may occur as the denaturing is removed. According to the present invention, in order to solve this problem associated with the refolding process, detergents are employed as artificial chaperons for preventing aggregation of protein. As a result of the detergents acting as artificial chaperons, the problem of protein aggregation, which may occur especially when diluting a denaturing agent in a highly excessive solution, can be solved.

As used herein, a "folded state" refers to a state in which a protein assumes a higher-order structure(s) which is necessary for exhibiting activity. "Refolding" or "folding again" refers to a protein which has once been denatured to lose or reduce its activity taking a folded state again so that the activity of the protein is restored.

When a solution containing a denatured protein and a solution containing a detergent are mixed, the denaturing agent coexisting with the denatured protein is diluted, and the detergent forms a protein-detergent complex with the denatured protein. As a result, the denatured protein is prevented from aggregating. As used herein, a "protein-detergent complex" refers to a complex in which a protein exists in a stable unfolded state due to the presence of a detergent in the vicinity of the protein; it is not required that chemical bonds be formed between the protein and the deterrent.

Next, from the protein-detergent complex (in which the protein is in an unfolded state), the detergent is removed so as to allow the protein to properly fold. High-molecular weight amylose is used as an artificial chaperon to serve this function. Due to its inclusion ability, high-molecular weight amylose takes in the detergent. As a result, the detergent is gradually removed from the protein-detergent complex, whereby activation of the denatured protein gradually occurs. That is, the protein is slowly refolded into a proper higher-order structure(s), thereby allowing its activity to be restored.

The high-molecular weight amylose to be used for the method according to the present invention can be suitably used for any denatured protein, irrespective of the kind of higher-order structure assumed by the denatured protein in a native state before denaturation, i.e., irrespective of the kind of denatured protein used.

As used herein, "high-molecular weight amylose" refers to straight-chain α-1,4-glucan preferably having an average polymerization degree of more than about 20, i.e., having an average molecular weight of more than about 3,500. The average molecular weight of high-molecular weight amylose is preferably about 10,000 to 3,000,000; more preferably about 20,000 to 2,000,000; and still more preferably about 600,000 to 1,100,000.

It is generally known that the amylose substantially changes its nature depending on the polymerization degree. For example, low-molecular weight amylose has a low solubility. Even if it dissolves at all, low-molecular weight amylose is known to quickly form an insoluble precipitation. On the other hand, high-molecular weight amylose has a high inclusion ability; its aqueous solution is stable; and it is slow to form any precipitation. Therefore, in practice, it would be desirable to test amylose of various molecular weights and select the type of amylose that proves the most effective. In particular, high-molecular weight amylose having an average molecular weight over about 600,000 can be especially suitably used for the present invention because such amylose exhibits solubility in water, and therefore is much easier to handle than insoluble, low-molecular weight amylose.

In the case where insoluble types of high-molecular weight amylose, i.e., those having a relatively low-molecular weight, are used, the high-molecular weight amylose can be used in the form of an inclusion compound in which a lower alcohol is included. As a result, the solubility of such high-molecular weight amylose can be improved.

Examples of lower alcohols to be used for the production of such an inclusion compound include: methanol, ethanol, 1-propanol, 2-propanol, 1-butanol, 2-butanol, 2-methy-2-propanol, 1-pentanol, 2-pentanol, 3-pentanol, 1-hexanol, 2-hexanol, 3-hexanol, and the like. The alcohol is preferably 1-propanol, 1-butanol, 1-pentanol, 1-hexanol, or the like, and more preferably 1-butanol or 1-pentanol. The solubility of amylose can be improved by including such an alcohol.

An amylose-alcohol inclusion compound in which an alcohol is included can be obtained by adding in appropriate amount of alcohol to an amylose-containing solution so as to allow crystals of the amylose-alcohol inclusion compound to form, recovering the resultant crystals through centrifugation, and drying the crystals. For example, by using 1-butanol, an amylose-butanol inclusion compound can be prepared as follows: to an amylose-containing solution, an about $\frac{1}{30}$ volume to an equivalent volume, preferably an about $\frac{1}{20}$ to about $\frac{1}{5}$ volume, and more preferably an about $\frac{1}{10}$ volume of 1-butanol is admixed, thereby allowing an amylose-butanol inclusion compound to precipitate; this precipitation may be recovered through centrifugation. After en amylose-butanol inclusion compound has been recovered through the first centrifugation, the amylose-butanol inclusion compound may be dissolved in hot water at about 30° C. to about 100° C., preferably about 60° C. to about 90° C. and 1-butanol may be again added. As a result, a purer amylose-butanol inclusion compound can be obtained.

The high-molecular weight amylose may be a synthetic amylose or a naturally-occurring amylose. Preferably, the high-molecular weight amylose is an amylose which has been synthesized by using an enzyme (e.g., phosphorylase). An enzymatically-synthesized amylose obtained through enzymatic synthesis using phosphorylase can be suitably used because of the satisfactory reproducibility of molecular weight distribution, ability to produce an amylose having a desired molecular weight, absence of impurities, and absence of branch structures associated with α-1,6-bonds.

High-molecular weight amylose can be synthesized by a method known in the art. For example, following the method of Kitamura et al. (Denpun Kagaku vol. 36, pp. 257–264, 1989), a reaction solution may be obtained by mixing glucose-1-phosphate and maltopentaose at various ratios in an appropriate solution in the presence of phosphorylase, and by incubating the resultant reaction solution for about 1 hour to several days at an appropriate temperature (e.g., about 30° C. to about 50° C.). The average molecular weight of the synthesized high-molecular weight amylose can be adjusted by appropriately varying the ratio between glucose-1-phosphate and maltopentaose. For example, when the molar ratio between glucose-1-phosphate and maltopentaose is in the range of about 1:0.01 to about 1:0.00011, the resultant high-molecular weight amylose can have an average molecular weight in the range of about 10,000 to about 1,000,000. After the reaction, the reaction solution is heated to inactivate phosphorylase. Next, centrifugation at about 10,000×g is typically performed for about 15 minutes, and the supernatant is recovered. Thus, the enzyme can be removed from the reaction solution.

The high-molecular weight amylose thus synthesized can be purified by various methods known in the art. For example, a lower alcohol is added to a supernatant from which enzymes have been removed, and after being left to stand at room temperature for about 12 hours, an amylose-lower alcohol inclusion compound may be allowed to recrystallize. Then, centrifugation at about 10,000×g is performed for about 15 minutes, and a precipitation of the amylose-lower alcohol inclusion compound may be recovered, and air-dried, whereby powder of the amylose-lower alcohol inclusion compound can be obtained. On the other hand, in order to obtain high-molecular weight amylose which is not in the form of an inclusion compound, a precipitation of the amylose-lower alcohol inclusion compound may be dissolved in hot water, and thereafter an equivalent amount of ethanol is added so as to allow amylose to precipitate. Then, centrifugation at about 10,000×g is typically performed for about 15 minutes. After repeating precipitation/wash with ethanol several times, the compound is lyophilized to give pure amylose.

The process of activation of a denatured protein according to the method of the present invention can be evaluated by measuring the protein activity. In the case where the protein is an enzyme, en enzymatic activity measurement method suitable for that enzyme is used. In the case where the protein is a bioactive polypeptide, any measurement method for the relevant bioactivity can be utilized.

When the method according to the present invention is used for the activation of a protein of interest from a denatured state in practice, it would be preferable to test various combinations of several detergents and high-molecular weight amylose of different molecular weights for optimum results. The protein refolding kit according to the present invention is aimed at facilitating this objective. Specifically, the protein refolding kit according to the present invention includes at least one (more preferably more then one) kind of detergent, and at least one (more preferably more than one) kind of high-molecular weight amylose. As detergent removing agents, it is possible to add cyclic α-1,4-glucan and/or low-molecular weight straight-chain α-1,4-glucan, etc., to the kit, in addition to high-molecular weight amylose. The protein refolding kit according to the present invention can be utilized for the refolding of a number of useful proteins in expression systems which are associated with problems such as inclusion body formation.

Hereinafter, the present invention will be described more specifically with respect to the following examples. However, the present invention is not limited to such examples.

In the following examples, three kinds of proteins having different secondary structures are intentionally used as model proteins, in order to show that the activation method according to the present invention is generically applicable to a large number of proteins, that is: citrate synthase, most of whose secondary structure in a native state is composed of α helix structural regions; carbonate dehydrogenase B about 80% of whose secondary structure in a native state is composed of β sheet structural regions; and lysozyme which includes both α helix structural regions and β sheet structural regions as well as intramolecular S—S bonds in a native state.

The α helix structure, the β sheet structure, and intramolecular S—S bonds which are included in the above three proteins are typical higher-order structures assumed by naturally-occurring proteins. Moreover, the above three proteins have a poor spontaneous folding ability and are not considered likely to assume a higher-order structure without the assistance of molecular chaperons or the like. Therefore, a method which is capable of folding these three model proteins from a denatured state into higher-order structures for exhibiting activity should be considered as generically applicable to a large number of proteins.

EXAMPLE 1

Preparation of High-molecular Weight Amylose

Following the method of Kitamura et al. (Denpun Kagaku vol. 36, pp. 257–264, 1989, supra), a high-molecular weight amylose was prepared as follows. Glucose-1-phosphate and maltopentaose were mixed in a 10 mM sodium maleate buffer (pH 6.0) in the presence of an enzyme phosphorylase (0.6 units/ml), and incubated for 18 hours at 35° C. Thus, an enzymatic reaction was carried out, whereby high-molecular weight amylose was synthesized. By varying the molar ratio between glucose-1-phosphate and maltopentaose so as to be 1:0.005, 1:0.001, 1:0.0003, or 1:0.00014, the average molecular weight of the high-molecular weight amylose synthesized with the above enzyme were adjusted to four levels, i.e., about 20,000, about 80,000, about 300,000, or about 700.000. After completing the enzymatic reaction, the reaction solution was heated to 90° C. for 10 minutes to inactivate the enzyme. Next, centrifugation at 10,000×g was performed for 15 minutes, and the supernatant was recovered. Thus, the inactivated enzyme was removed.

To the resultant supernatant, a 1/10 volume of 1-butanol was added and left to stand at room temperature for 18 hours, thereby allowing crystals of an amylose-butanol inclusion compound to form. This amylose-butanol inclusion compound is an inclusion compound of amylose including 1-butanol. A centrifugation at 10,000×g was performed for 15 minutes, and the precipitation was recovered. The precipitation was dissolved in hot water at 90° C. To the solution with the precipitation dissolved therein, a 1/10 volume of 1-butanol was again added and left to stand at room temperature for 18 hours, thereby recrystallizing the amylose-butanol inclusion compound. A centrifugation at 10,000×g was performed for 15 minutes, and the precipitation of the amylose-butanol inclusion compound was recovered. The precipitation was suspended in a small amount of saturated 1-butanol aqueous solution.

As for the amylose having an average molecular weight of about 700,000, a precipitation of an amylose-butanol inclusion compound was dissolved in hot water at 90° C. Thereafter, an equivalent amount of ethanol was added so as to allow amylose to precipitate. A centrifugation at 10,000×g was performed for 15 minutes, and the precipitate was further subjected to several repetitions of precipitation/wash with ethanol, and thereafter lyophilized. Thus, a non-inclusion form of amylose powder was obtained.

EXAMPLE 2

Denaturation and Activation of Citrate Synthase (CS)1

(1) Preparation of a Denatured CS Solution

A 3.2 M ammonium sulfate suspension (Boehringer Mannheim GmbH) containing citrate synthase (CS) was added to an aqueous solution of guanidine hydrochloride containing dithiothreitol, thereby obtaining a mixture solution. The mixture solution had a CS concentration of 2.4 mg/ml, a guanidine hydrochloride concentration of 6 M, and a dithiothreitol concentration of 40 mM. This mixture solution was allowed to react at 25° C. for 1 hour, thereby destroying the higher-order structure(s) of CS. Thus, a denatured CS solution, in which the enzymatic activity of CS was completely lost, was obtained.

(2) Activation of Denatured CS

To 1 unit volume of the denatured CS solution described in (1) above, 70 unit volumes of an aqueous solution of a detergent which was prepared on use (0.1 wt % Tween 40, 0.71 mM EDTA, 145 mM Tris•HCl(pH 7.6)) was added, and left to stand at room temperature for 1 hour, thereby allowing a detergent-CS complex to form. Thus, a detergent-CS complex solution was obtained. To 80 unit volumes of the detergent-CS complex solution, 20 unit volumes of an aqueous solution (5 wt %) of high-molecular weight amylose (obtained according to Example 1 above; having an average molecular weight of about 700,000) was added. The solution was allowed to react at 25° C. for 2 hours, thereby allowing CS to be folded again and activated. After completing the 2 hours of reaction, the resultant reaction solution was passed through a cellulose acetate filter (pore size: 0.2 μm) as a pretreatment, whereby the aggregates within the reaction solution were removed, leaving a filtrate. An enzymatic activity in the resultant filtrate was measured according to (3) below.

(3) Measurement of Enzymatic Activity of CS

Twenty microliters of the filtrate, containing refolded CS as obtained according to (2) above, was added to 380 μl of a reaction solution in which acetyl CoA and oxaloacetic acid had been dissolved as substrates. Thus, 400 μl of a solution for enzymatic activity measurement was prepared. The absorbance (at 412 nm) of the solution for enzymatic activity measurement at 25° C. was measured using a spectrophotometer, at intervals of every 0.5 seconds for a total duration of 60 seconds, after the solution was prepared. From the absorbance measurements, the initial reaction rate of the enzymatic reaction was calculated. The initial reaction rate of the enzymatic reaction was used as an index representing enzymatic activity. The composition of the reaction solution was as follows (final concentrations in the solution for enzymatic activity measurement; the solvent was water): 158 mM Tris•HCl (pH 7.6), 0.022 mM acetyl CoA, 0.48 mM oxaloacetic acid, and 0.48 mM dithiobis.

The enzymatic activity was expressed in percentage against the enzymatic activity (defined as 100%) of undenatured CS which was diluted with the aforementioned reaction solution to the same concentration.

(4) Results

It was indicated that the CS activity, which had been lost by 100% through denaturation, was restored by 100% by the activation method according to the present example of the invention.

EXAMPLE 3

Denaturation and Activation of CS2

Denatured CS was activated through the same operation as described In Example 2, except that Tween 60 was used as a detergent.

As a result, it was indicated that the CS activity, which had been lost by 100% through denaturation, was restored by 100% by the activation method according to the present example of the invention.

EXAMPLE 4

Denaturation and Activation of Carbonate Dehydrogenase B (CAB)1

(1) Preparation of a Denatured CAB Solution

An aqueous solution (30 mg/ml) of CAB (Sigma) was added to an aqueous solution of 6 M guanidine hydrochloride. The resultant solution was allowed to react at 25° C. for 16 hours, thereby destroying the higher-order structure(s) of CAB. Thus, a denatured CAB solution, in which the enzymatic activity of CAB was completely lost, was obtained.

(2) Activation of Denatured CAB

To 1 unit volume of a denatured CAB solution prepared according to (1) above, 700 unit volumes of a freshly-prepared aqueous solution of a detergent (0.1 wt % CTAB, 23 mM Tris sulfate buffer (pH 7.8)) was added, and left to stand at room temperature for 10 minutes, thereby allowing a detergent-CAB complex to form. Thus, a detergent-CAB complex solution was obtained.

Next, to 35 unit volumes of the detergent-CAB complex solution, 15 unit volumes of an aqueous solution of a separately prepared aqueous solution of high-molecular weight amylose (obtained according to Example 1 above; having an average molecular weight of about 700,000) was added (final concentration: 0.9 wt %). The solution was allowed to react at 25° C. overnight, thereby allowing CAB to be folded again and activated.

After completing the overnight reaction, the resultant reaction solution was passed through a cellulose acetate filter (pore size: 0.2 $\mu$m) as a pretreatment, whereby the aggregates within the reaction solution were removed, leaving a filtrate. An enzymatic activity in the resultant filtrate was measured according to (3) below.

(3) Measurement of Enzymatic Activity of CAB

Four-hundred fifty microliters of the filtrate, containing refolded CAB as obtained according to (2) above, was added to 50 $\mu$l of a reaction solution to which paranitrophenylacetate (pNPAC) had been dissolved as a substrate. Thus, 500 $\mu$l of a solution for enzymatic activity measurement was prepared. The absorbance (at 400 nm) of the solution for enzymatic activity measurement at 25° C. was measured using a spectrophotometer at intervals of every 0.5 seconds for a total duration of 60 seconds, after the solution was prepared. From the absorbance measurements, the initial reaction rate of the enzymatic reaction was calculated. The Initial reaction rate of the enzymatic reaction was used as an index representing enzymatic activity. The composition of the reaction solution was as follows (final concentrations in the solution for enzymatic activity measurement; the solvent was water): 52 mM pNPAC and 23 mM Tris-sulfate buffer (pH 7.8).

The enzymatic activity was expressed in percentage against the enzymatic activity (defined as 100%) of undenatured CAB which was diluted with the aforementioned reaction solution to the same concentration.

(4) Results

It was indicated that the CAB activity, which had been lost by 100% through denaturation, was restored by 100% by the activation method according to the present example of the invention.

EXAMPLE 5

Denaturation and Activation of CAB 2

Denatured CAB was activated through the same operation as described in Example 4, except that SB3-14 was used as a detergent.

As a result, it was indicated that the CAB activity, which had been lost by 100% through denaturation, was restored by 100% by the activation method according to the present example of the invention.

EXAMPLE 6

Denaturation and Activation of CAB 3

Denatured CAB was activated through the same operation as described in Example 4, except that an amylose-butanol inclusion compound having an average molecular weight of about 20,000 was used as the high-molecular weight amylose, and that the final concentration of the high-molecular weight amylose in the reaction solution was 0.2 wt %.

As a result, it was indicated that the CAB activity, which had been lost by 100% through denaturation, was restored by 100% by the activation method according to the present example of the invention.

EXAMPLE 7

Denaturation and Activation of CAB 4

Denatured CAB was activated through the same operation as described in Example 6, except that SB3-14 was used as a detergent.

As a result, it was indicated that the CAB activity, which had been lost by 100% through denaturation, was restored by 80% by the activation method according to the present example of the invention.

EXAMPLE 8

Denaturation and Activation of Lysozyme 1

(1) Preparation of a Denatured Lysozyme Solution

An aqueous solution of lysozyme was added to an aqueous solution of guanidine hydrochloride containing dithiothreitol, thereby obtaining a mixture solution. The mixture solution had a lysozyme concentration of 15 mg/ml, a guanidine hydrochloride concentration of 5 M, and a dithiothreitol concentration of 50 mM. This mixture solution was allowed to react at 25° C. for 16 hours, thereby destroying the higher-order structure(s) of lysozyme. Thus, a denatured lysozyme solution, in which the enzymatic activity of lysozyme was completely lost, was obtained.

(2) Activation of Denatured Lysozyme

To 1 unit volume of a denatured lysozyme solution obtained according to (1) above, 100 unit volumes of a freshly-prepared aqueous solution of a detergent (0.1 wt % CTAB, 2 mM DL-cystine, 23 mM Tris acetate buffer (pH 8.1)) was added, and allowed to stand at room temperature overnight, thereby allowing a detergent-lysozyme complex to form. Thus, a detergent-lysozyme complex solution was obtained.

Next, to 140 unit volumes of the detergent-lysozyme complex solution, 60 unit volumes of a separately prepared aqueous solution of high-molecular weight amylose (obtained according to Example 1 above; having an average molecular weight of about 700,000) was added (final concentration: 0.9 wt %). The solution was allowed to react at 25° C. for 1 hour, thereby allowing lysozyme to be folded again and activated. After completing the one-hour reaction, the resultant reaction solution was passed through a cellulose acetate filter (pore size: 0.2 $\mu$m) as a pretreatment, whereby the aggregates within the reaction solution were removed, leaving a filtrate. An enzymatic activity in the resultant filtrate was measured according to (3) below, (3) Measurement of Enzymatic Activity of Lysozyme Twenty microliters of the filtrate, containing refolded lysozyme as obtained according to (2) above, was added to 500 µl of a reaction solution in which Micrococcus lysodeikticus had been suspended as a substrate. Thus, 520 µl of a solution for enzymatic activity measurement was prepared. The absorbance (at 450 nm) of the solution for enzymatic activity measurement at 25° C. was measured using a spectrophotometer at intervals of every 0.5 seconds for a total duration of 60 seconds, after the solution was prepared. From the absorbance measurements, the initial reaction rate of the enzymatic reaction was calculated. The initial reaction rate of the enzymatic reaction was used as an index representing enzymatic activity. The composition of the reaction solution was as follows (final concentrations in the solution for enzymatic activity measurement; the solvent was water): 0.16 mg/ml Micrococcus lysodeikticus and 50 mM phosphate buffer (pH 6.2).

The enzymatic activity was expressed in percentage against the enzymatic activity (defined as 100%) of undenatured lysozyme which was diluted with the aforementioned reaction solution to the same concentration.

(4) Results

It was indicated that the lysozyme activity, which had been lost by 100% through denaturation, was restored by 80% by the activation method according to the present example of the invention.

EXAMPLE 9

Denaturation and Activation of Lysozyme 2

Denatured lysozyme was activated through the same operation as described in Example 8, except that SB3-14 was used as a detergent.

As a result, it was indicated that the lysozyme activity, which had been lost by 100% through denaturation, was restored by 80% by the activation method according to the present example of the invention.

EXAMPLE 10

Denaturation of Lysozyme, and Activation thereof Utilizing a Butanol Inclusion Compound 3

Denatured lysozyme was activated through the same operation as described in Example 9, except that three different amylose-butanol inclusion compounds having average molecular weights of about 20,000, about 80,000, or about 300,000 were used as the high-molecular weight amylose, and that concentration of the high-molecular weight amylose in the reaction solution was 0.9 wt %, regardless of which amylose-butanol inclusion compound was used.

As a result, it was indicated that the lysozyme activity, which had been lost by 100% through denaturation, was restored by 70% by the activation method according to the present example of the invention, regardless of the molecular weight of the amylose used.

EXAMPLE 11

Comparison of Effects of High-Molecular Weight Amylose Against Low-Molecular Weight Amylose Denatured lysozyme was activated through the same operation as described in Example 9, except that three different amylose-butanol inclusion compound having average molecular weights of about 2,900, about 700,000, or about 20,000 were used as the amylose, and that the final concentration was 0.9 wt %. The amylose-butanol Inclusion compounds whose average molecular weights was about 2,900 was used as a low-molecular weight amylose for comparison purposes.

As a result, it was indicated that the activity level obtained with low-molecular weight amylose was 50% after performing an activation process for 180 minutes. On the other hand, the activity level obtained with high-molecular weight amylose having an average molecular weight of about 700,000 or about 20,000 was 80% or 70%, respectively, after performing an activation process for 180 minutes.

FIG. 2 is a graph illustrating changes in the activation of denatured lysozyme over time The two kinds of high-molecular weight amylose showed a higher level of activation than the low-molecular weight amylose.

According to the present invention, it is possible to fold a denatured protein, where the protein may have a poor spontaneous folding ability and have difficulties in assuming a proper higher-order structure without the assistance of molecular chaperons, such that the protein in a relatively short time so as to assume a proper higher-order structure for acquiring activity. Moreover, according to the present invention, there is provided a protein refolding kit which is useful for facilitating the method according to the present invention, the kit including at least one kind of high-molecular weight amylose and at least one kind of detergent. Each element of the kit can be provided in large quantities and with equal qualities.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for activating a denatured protein, comprising the steps of:
    adding a detergent to the denatured protein to allow a protein-detergent complex to be formed;
    adding a high-molecular weight amylose to the protein-detergent complex so that the high-molecular weight amylose removes the detergent thereby allowing the protein to be folded again into a higher-order structure for acquiring activity, thus activating the protein; and,
    recovering the activated protein.

2. A method according to claim 1,
    further comprising the step of adding a denaturing agent to the denatured protein to cause the denatured protein to be in an unfolded state,
    wherein the step of adding the denaturing agent is performed before the step of adding the detergent to the denatured protein.

3. A method according to claim 1, wherein the high-molecular weight amylose is an inclusion compound which includes a lower alcohol.

4. A method according to claim 3, wherein the lower alcohol is butanol.

5. A method according to claim 1, wherein the high-molecular weight amylose has an average molecular weight in the range of about 10,000 to about 20,000,000.

6. A method according to claim 5, wherein the high-molecular weight amylose has an average molecular weight in the range of about 20,000 to about 11,000,000.

7. A method according to claim 1, wherein the high-molecular weight amylose is an amylose which is synthesized by using an enzyme.

8. A method according to claim 1, wherein the detergent is selected from the group consisting of:

polyoxyethylene sorbitan ester, polyoxyethylene dodecyl ether, polyoxyethylene fatty acid ester, sucrose fatty acid ester, cetyltrimethylammonium bromide, sodium deoxycholate, hexadecyltrimethylammonium bromide, and myristylsulfobetaine.

9. A method according to claim 1, wherein the denatured protein includes an α helix structural region.

10. A method according to claim 1, wherein the denatured protein includes a β sheet structural region.

11. A method according to claim 1, wherein the denatured protein includes an intramolecular S—S bond.

12. A method for activating a denatured protein including a helix structural region, comprising the steps of:

adding an excess of a polyoxyethylene type detergent to the denatured protein to allow a protein-detergent complex to be formed, thereby preventing aggregation of the protein;

adding a high-molecular weight amylose to the protein-detergent complex so that the high-molecular weight amylose removes the detergent, thereby allowing the protein to be folded again into a higher-order structure for acquiring activity, thus activating the protein; and, recovering the activated protein.

13. A method according to claim 12, wherein the polyoxyethylene type detergent is selected from the group consisting of:

polyoxyethylene sorbitan ester, polyoxyethylene dodecyl ether, polyoxyethylene fatty acid ester, and sucrose fatty acid ester.

14. A method for activating a denatured protein including a β sheet structural region, comprising the steps of:

adding an excess of an ionic type detergent to the denatured protein to allow a protein-detergent complex to be formed, thereby preventing aggregation of the protein;

adding high-molecular weight amylose to the protein-detergent complex so that the high-molecular weight amylose removes the detergent, thereby allowing the protein to be folded again into a higher-order structure for acquiring activity, thus activating the protein; and recovering the activated protein.

15. A method for activating a denatured protein including an intramolecular S—S bond, comprising the steps of:

adding an excess of an ionic type detergent to the denatured protein to allow a protein-detergent complex to be formed, thereby preventing aggregation of the protein;

adding high-molecular weight amylose to the protein-detergent complex so that the high-molecular weight amylose removes the detergent, thereby allowing the protein to be folded again into a higher-order structure for acquiring activity, thus activating the protein; and recovering the activated protein.

16. A method according to claim 14, wherein the ionic type detergent is selected from the group consisting of:

cetyltrimethylammonium bromide, sodium deoxycholate, hexadecyltrimethylammonium bromide, and myristylsulfobetaine.

17. A method according to claim 15, wherein the ionic type detergent Is selected from the group consisting of:

cetyltrimethylammonium bromide, sodium deoxycholate, hexadecyltrimethylammonium bromide, and myristylsulfobetaine.

* * * * *